United States Patent
Kim et al.

(10) Patent No.: US 11,407,882 B2
(45) Date of Patent: *Aug. 9, 2022

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/737,686

(22) PCT Filed: Apr. 17, 2017

(86) PCT No.: PCT/KR2017/004117
§ 371 (c)(1),
(2) Date: Dec. 18, 2017

(87) PCT Pub. No.: WO2017/183876
PCT Pub. Date: Oct. 26, 2017

(65) Prior Publication Data
US 2018/0171103 A1  Jun. 21, 2018

(30) Foreign Application Priority Data

Apr. 22, 2016 (KR) .................. 10-2016-0049081
Apr. 13, 2017 (KR) .................. 10-2017-0047831

(51) Int. Cl.
| | |
|---|---|
| C08K 5/12 | (2006.01) |
| C07C 69/75 | (2006.01) |
| C08K 5/092 | (2006.01) |
| C07C 67/62 | (2006.01) |
| C08K 5/11 | (2006.01) |
| C08K 5/1515 | (2006.01) |
| C08K 9/04 | (2006.01) |
| C08K 5/00 | (2006.01) |

(52) U.S. Cl.
CPC .............. C08K 5/12 (2013.01); C07C 67/62 (2013.01); C07C 69/75 (2013.01); C08K 5/092 (2013.01); C08K 5/11 (2013.01); C08K 5/1515 (2013.01); C08K 9/04 (2013.01); C08K 5/0016 (2013.01); C08K 2201/014 (2013.01)

(58) Field of Classification Search
CPC . C08K 5/12; C08K 5/092; C08K 5/11; C08K 5/1515; C08K 5/0016; C08K 2201/014; C08K 9/04; C07C 67/62; C07C 69/75; C09K 9/04

USPC .............................................. 524/285
See application file for complete search history.

(56) References Cited

U.S. PATENT DOCUMENTS

| | | | |
|---|---|---|---|
| 8,283,411 B2 | 10/2012 | Gosse et al. | |
| 8,299,292 B2 * | 10/2012 | Yoon .................. | C07C 69/75 560/127 |
| 2005/0020718 A1 | 1/2005 | Gosse et al. | |
| 2007/0037926 A1 | 2/2007 | Olsen et al. | |
| 2007/0287781 A1 * | 12/2007 | Grass .................. | C07C 69/67 524/308 |
| 2007/0293646 A1 | 12/2007 | Gosse et al. | |
| 2008/0274364 A1 | 11/2008 | Gosse et al. | |
| 2009/0291304 A1 | 11/2009 | Gosse et al. | |
| 2011/0040001 A1 | 2/2011 | Gosse et al. | |
| 2011/0046283 A1 | 2/2011 | Grass et al. | |
| 2012/0071598 A1 | 3/2012 | Gosse et al. | |
| 2013/0137789 A1 | 5/2013 | Olsen et al. | |
| 2013/0225737 A1 | 8/2013 | Gosse et al. | |
| 2016/0326346 A1 | 11/2016 | Gourdin et al. | |

FOREIGN PATENT DOCUMENTS

| | | | | |
|---|---|---|---|---|
| CN | 103965564 A | | 8/2014 | |
| EP | 0138147 A2 * | | 4/1985 | ............... C08K 5/11 |
| EP | 2810982 A1 | | 12/2014 | |
| EP | 3211029 A1 | | 8/2017 | |
| KR | 10-2009-0038514 A | | 4/2009 | |
| KR | 10-2016-0047221 A | | 5/2016 | |
| KR | 2016-0134573 A | | 11/2016 | |
| WO | 2013/004265 A1 | | 1/2013 | |
| WO | 2015/101569 A1 | | 7/2015 | |
| WO | WO-2015101569 A1 * | | 7/2015 | ............... C08J 3/18 |
| WO | 2015/147300 A1 | | 10/2015 | |
| WO | 2016-064125 A1 | | 4/2016 | |

OTHER PUBLICATIONS

KR 2009-0038514 A, machine translation, EPO espacenet. (Year: 2009).*
XP 002779558, Database WPI Week 201683, Thomson Scientific, London, GB; AN 2016-737334; pp. 1-2 (Corresponding KR 10-2016-0134573A (published Nov. 23, 2016)).

* cited by examiner

*Primary Examiner* — Josephine L Chang
(74) *Attorney, Agent, or Firm* — Dentons US LLP

(57) ABSTRACT

Provided are a plasticizer composition, a resin composition and a method of preparing the same. Particularly, a plasticizer comprising a cyclohexane 1,4-diester based material and a citrate-based material. The plasticizer is capable of improving physical properties such as plasticization efficiency, migration, tensile strength, elongation rate, stress migration and light fastness, which are required for sheet formulations, when used as a plasticizer for the resin composition by improving poor physical properties generated due to a structural limitation thereof, and a resin composition including the same are provided.

14 Claims, 1 Drawing Sheet

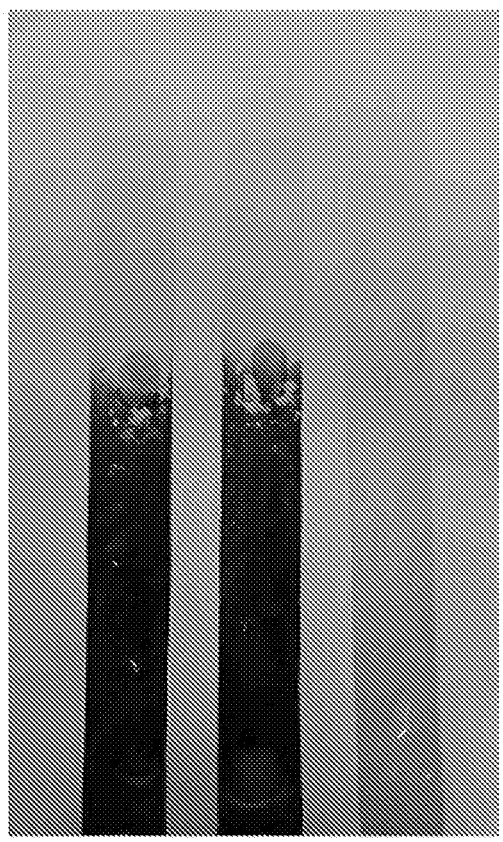

PLASTICIZER COMPOSITION AND RESIN COMPOSITION INCLUDING THE SAME

CROSS-REFERENCE TO RELATED APPLICATION

This application is a National Stage Application of International Application No. PCT/KR2017/004117 filed on Apr. 17, 2017, which claims the benefit of Korean Patent Application No. 10-2016-0049081 filed on Apr. 22, 2016 and Korean Patent Application No. 10-2017-0047831 filed on Apr. 13, 2017, all of which are hereby incorporated by reference in their entirety for all purposes as if fully set forth herein.

BACKGROUND

1. Field of the Invention

The present invention relates to a plasticizer composition and a resin composition comprising the same.

2. Discussion of Related Art

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Meanwhile, there is an increasing demand for environmentally friendly products relating to flooring materials, wallpaper, soft and hard sheets, etc. obtained in the plastisol industry, the calendering industry, the extruding/injecting compound industry, etc., and in order to reinforce quality characteristics, processability and productivity of each end product for such environmentally friendly products, suitable plasticizers have to be used depending on discoloration, migration, mechanical properties, etc.

Depending on properties required by industry in various areas of use, such as tensile strength, an elongation rate, light fastness, a migration property, gelability or an absorption rate, a PVC resin is mixed with a supplementary material such as a plasticizer, a filler, a stabilizer, a viscosity depressant, a dispersant, an antifoaming agent or a foaming agent.

As an example, among plasticizer compositions applicable to PVC, when di(2-ethylhexyl)terephthalate which is relatively cheap and most widely used is applied, a plasticizer exhibits high hardness or sol viscosity, a relatively low absorption rate, and poor migration and stress migration.

To improve these physical properties, a hydrogenated material of di(2-ethylhexyl)terephthalate may be considered. However, the hydrogenated material may improve plasticization efficiency, but may impart poor migration or thermal stability, and is accompanied by an increase in production cost caused by hydrogenation, and therefore it is difficult to ensure economic feasibility.

To overcome such a problem, there is a consistent demand for developing a new composition product including a material which has physical properties superior to the hydrogenated di(2-ethylhexyl)terephthalate, such as di(2-ethylhexyl) 1,4-cyclohexanoate, or a new derivative thereof, and research on developing products and their use as environmentally friendly plasticizers for vinyl chloride-based resins is progressing.

SUMMARY OF THE INVENTION

The present invention provides a plasticizer used in a resin composition, which can improve physical properties such as plasticization efficiency, migration, gelability, etc., required in formulations for a calendering sheet, plastisol, extrusion/injection compounds, etc., a method of preparing the same, and a resin composition including the same.

Specifically, based on the ideas that migration can be improved when a citrate-based plasticizer is mixed at a certain amount to solve the problems of migration and volatile loss, and economic feasibility of hydrogenated di(2-ethylhexyl)terephthalate, and when a hydrogenated single material is mixed, the use of an alkyl group having 9 or 10 carbon atoms provides excellent tensile strength, elongation rate, volatile loss, migration, plasticizer absorption rate and stress migration, the present invention is directed to providing a plasticizer composition, which includes one kind of 1,4-cyclohexane diester-based material and a citrate-based material.

In one aspect, according to an exemplary embodiment of the present invention, a plasticizer composition which includes one kind of cyclohexane 1,4-diester-based material and a citrate-based material is provided, and a weight ratio of the cyclohexane 1,4-diester-based material and the citrate-based material is from 99:1 to 1:99.

The citrate-based material may include any one selected from the group consisting of hybrid C4-C10 alkyl substituted citrate-based materials and non-hybrid C4-C10 alkyl substituted citrate-based materials.

The plasticizer composition may further include an epoxidized material.

The epoxidized material may be further included at 1 to 100 parts by weight based on 100 parts by weight of the sum of the cyclohexane 1,4-diester-based material and the citrate-based material.

In another aspect, according to an exemplary embodiment of the present invention, a method of preparing a plasticizer composition is provided, the method comprising: preparing a cyclohexane 1,4-diester-based material by hydrogenating a terephthalate-based material in the presence of a metal catalyst; and blending the cyclohexane 1,4-diester-based material and a citrate-based material at a weight ratio of 99:1 to 1:99 to obtain a plasticizer composition, and the terephthalate-based material is a mixture.

In still another aspect, according to an exemplary embodiment of the present invention, a resin composition which includes 100 parts by weight of a resin; and 5 to 150 parts by weight of claim 1 is provided.

The resin may include one or more selected from the group consisting of ethylene vinyl acetate, polyethylene, polypropylene, polyketone, polyvinyl chloride, polystyrene, polyurethane, and a thermoplastic elastomer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawing, in which:

FIG. 1 is an image indicating the improvement in thermal resistance according to addition of an epoxidized material.

DETAILED DESCRIPTION OF EXEMPLARY EMBODIMENTS

Hereinafter, to help in understanding the present invention, the present invention will be described in further detail.

It should be noted that terms and words used herein and in the claims should not be interpreted as being limited to a conventional or literal meaning, but should be interpreted with meanings and concepts which are consistent with the technological scope of the invention based on the principle that the inventors have appropriately defined concepts of terms in order to describe the invention in the best way.

The term "butyl" used herein refers to an alkyl group having 4 carbon atoms, and includes both linear and branched chains. For example, the butyl may be n-butyl, isobutyl, or t-butyl, and preferably, n-butyl or isobutyl.

The terms "octyl" and "2-ethylhexyl" used herein refer to an alkyl group having 8 carbon atoms, and as octyl is an abbreviation of 2-ethylhexyl, may be mixed. Therefore, in some cases, these terms may mean octyl, which is a linear alkyl group, but may also be interpreted to mean 2-ethylhexyl, which is a branched alkyl group.

Plasticizer Composition

According to an exemplary embodiment of the present invention, a plasticizer composition including one kind of cyclohexane 1,4-diester-based material may be provided. Specifically, the cyclohexane 1,4-diester-based material may be included in an amount of 1 to 99 wt %, 20 to 99 wt %, 40 to 99 wt %, 50 to 95 wt % or 60 to 90 wt % based on a total weight of the composition.

In the specification, the cyclohexane 1,4-diester-based material may be, for example, when $R_1$ and $R_2$ are the same, named dialkyl cyclohexane-1,4-diester.

The cyclohexane 1,4-diester-based material may be selected from the group consisting of diisononyl cyclohexane-1,4-diester (1,4-DINCH), diisodecyl cyclohexane-1,4-diester (1,4-DIDCH), and di(2-propylheptyl) cyclohexane-1,4-diester (1,4-DPHCH).

As such, when the alkyl group binding to the diester has 9 or more carbon atoms, and preferably 9 or 10 carbon atoms, migration and volatile loss may be improved, and this is advantageous in terms of mechanical properties.

According to another exemplary embodiment of the present invention, the plasticizer composition may include a citrate-based material, and the citrate-based material may include one or more compounds selected from the group consisting of hybrid C4-C10 alkyl substituted citrate-based materials and non-hybrid C4-C10 alkyl substituted citrate-based materials.

The hybrid C4-C10 alkyl substituted citrate-based materials may include, for example, a citrate having combined substituents of C4 and C8 alkyl groups such as 1,2-dibutyl 3-(2-ethylhexyl) 2-hydroxypropane-1,2,3-tricarboxylate, 1,3-dibutyl 2-(2-ethylhexyl) 2-hydroxypropane-1,2,3-tricarboxylate, 1-butyl 2,3-di(2-ethylhexyl) 2-hydroxypropane-1,2,3-tricarboxylate, or 2-butyl 1,3-di(2-ethylhexyl) 2-hydroxypropane-1,2,3-tricarboxylate; and a citrate having combined substituents of C5 and C7 alkyl groups such as 1,2-dipentyl 3-heptyl 2-hydroxypropane-1,2,3-tricarboxylate, 1,3-dipentyl 2-heptyl 2-hydroxypropane-1,2,3-tricarboxylate, 1-pentyl 2,3-diheptyl 2-hydroxypropane-1,2,3-tricarboxylate, or 2-butyl 1,3-diheptyl 2-hydroxypropane-1,2,3-tricarboxylate. In addition, a citrate having combined substituents of two alkyl groups having different quantities of carbon atoms, which are selected from 4 to 10 carbon atoms, may be applied, and the alkyl groups may be linear or branched.

The non-hybrid C4-C10 alkyl substituted citrate-based materials may be linear or branched C4 to C10 alkyl substituted citrate-based materials. And for example, the linear or branched C4 to C10 alkyl group substituted citrate-based materials may be tributyl citrate (TBC), tripentyl citrate (TPC), trihexyl citrate (THC), triheptyl citrate (THPC), tri(2-ethylhexyl) citrate (TOC), trinonyl citrate (TNC), and tri(2-propylheptyl) citrate (TPHC). The butyl group or nonyl group may include structural isomers thereof, and for example, the butyl group may include an isobutyl group, the 2-ethylhexyl group may include an octyl group, the nonyl group may include an isononyl group, and the 2-propylheptyl group may include an isodecyl group.

Although not limited, the non-hybrid C4-C10 alkyl substituted citrate-based materials may be preferable to the hybrid alkyl substituted citrate-based material, and tributyl-citrate and/or tri(2-ethylhexyl)citrate may be used a little more often.

Meanwhile, a trialkyl citrate such as the hybrid or non-hybrid alkyl substituted citrate compound, or di n-alkyl-m-alkyl citrate may be applied, and when an acetyl group is present in the citrate-based material, physical properties of the plasticizer, particularly, processability and gelability, caused by a decrease in plasticization efficiency, may be degraded.

In other words, when the citrate-based material is an acetyl citrate compound in which hydrogen of remaining hydroxyl groups, other than three ester groups, is substituted with an acetyl group, due to problems of reduced plasticization efficiency, addition of an increased amount of a plasticizer to overcome the reduced plasticization efficiency, and an increased price of a product thereby, various aspects such as marketability, economic feasibility and physical properties may deteriorate.

Here, in the plasticizer composition, the upper limit of the weight ratio of the cyclohexane 1,4-diester-based material to the citrate-based material may be 99:1, 95:5, 90:10, 85:15, 80:20, 70:30 or 60:40, and the lower limit thereof may be 1:99, 5:95, 10:90, 15:85, 20:80, 30:70 or 40:60. The weight ratio is preferably from 90:10 to 20:80, and more preferably 90:10 to 30:70.

The plasticizer composition may include the cyclohexane 1,4-diester-based material and the citrate-based material, and further include an epoxidized material.

The plasticizer composition including the cyclohexane 1,4-diester-based material and the citrate-based material may not exhibit relatively lower thermal resistance among various physical properties, and such thermal resistance can be compensated by the addition of the epoxidized material.

An amount of the epoxidized material added to compensate the thermal resistance may be 1 to 100 parts by weight, and preferably, 5 to 80 parts by weight, based on 100 parts by weight of the sum of the cyclohexane 1,4-diester-based material and the citrate-based material. When the epoxidized material is added in the above range, the thermal resistance may be compensated. But when too much of the epoxidized material is added and exceeds 100 parts by weight, relatively less of the cyclohexane 1,4-diester-based material and the citrate-based material is included. And therefore there is a risk of fundamental physical properties of the plasticizer being degraded. For this reason, it is necessary to control the amount of the epoxidized material.

The epoxidized material may be, for example, epoxidized soybean oil, epoxidized castor oil, epoxidized linseed oil, epoxidized palm oil, an epoxidized stearate, an epoxidized oleate, an epoxidized tallate, an epoxidized linoleate or a mixture thereof. The epoxidized material is preferably epoxidized soybean oil (ESO), epoxidized linseed oil (ELO) or an epoxidized ester derivative thereof, but the present invention is not limited thereto.

Method of Preparing Plasticizer Composition

According to an exemplary embodiment of the present invention, a method of preparing a plasticizer composition includes: preparing a cyclohexane 1,4-diester-based material by hydrogenating a terephthalate-based material in the presence of a metal catalyst; and blending the cyclohexane 1,4-diester-based material and a citrate-based material at a weight ratio of 99:1 to 1:99 to obtain a plasticizer composition.

The terephthalate-based material may be prepared through direct esterification of one or more alcohols selected from the group consisting of 2-ethylhexyl alcohol, isononyl alcohol, 2-propylheptyl alcohol, butyl alcohol and isobutyl alcohol, and terephthalic acid.

The direct esterification may be performed by adding terephthalic acid to an alcohol and then reacting the resulting mixture in the presence of a catalyst under a nitrogen atmosphere; removing an unreacted alcohol and neutralizing an unreacted acid; and performing dehydration and filtration through vacuum distillation.

The alcohol may be included at 150 to 500 mol %, 200 to 400 mol %, 200 to 350 mol %, 250 to 400 mol %, or 270 to 330 mol % based on 100 mol % of terephthalic acid.

Meanwhile, the catalyst may be, for example, one or more selected from acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfate, etc., metal salts such as aluminum sulfate, lithium fluoride, potassium chloride, cesium chloride, calcium chloride, iron chloride, aluminum phosphate, etc., metal oxides such as heteropolyacid, etc., natural/synthetic zeolites, cation and anion exchange resins, and organic metals such as tetraalkyl titanate and polymers thereof, etc. As a specific example, the catalyst may be tetraalkyl titanate.

An amount of the catalyst used may depend on its type, and for instance, an amount of a homogeneous catalyst may be in the range of 0.01 to 5 wt %, 0.01 to 3 wt %, 1 to 5 wt % or 2 to 4 wt % based on total 100 wt % of the reactants, and an amount of a heterogeneous catalyst may be in the range of 5 to 200 wt %, 5 to 100 wt %, 20 to 200 wt %, or 20 to 150 wt % based on a total weight of the reactants.

The direct esterification may be performed at 80 to 270° C., and preferably, 150 to 250° C. for 10 minutes to 10 hours, preferably, 30 minutes to 8 hours, and more preferably 1 to 6 hours. In consideration of the boiling point of an alcohol, a terephthalate-based material may be effectively obtained in the ranges of suitable temperatures, catalysts, and time.

The hydrogenation may be a process for converting a terephthalate-based material into a cyclohexane 1,4-diester-based material by hydrogenation of the terephthalate-based material in the presence of a metal catalyst.

The hydrogenation may be a reaction for eliminating the aromaticity of benzene rings of the terephthalate-based materials by adding hydrogen in the presence of a metal catalyst, which may be a type of reduction.

The hydrogenation is for synthesizing a cyclohexane 1,4-diester-based material by reacting the terephthalate-based material with hydrogen in the presence of a metal catalyst, and conditions for this reaction may include all conventional reaction conditions for hydrogenating only benzene rings without affecting carbonyl groups substituted in the benzene.

The hydrogenation may be performed with an additional organic solvent such as ethanol or the like, but the present invention is not limited thereto. The metal catalyst may be an Rh/C catalyst, a Pt catalyst, a Pd catalyst or the like, which is generally used to hydrogenate a benzene ring, and any one capable of being used in the hydrogenation may be used without limitation.

For example, in the hydrogenation, a pressure for adding hydrogen may be approximately 3 to 15 MPa, and the reaction may be performed for approximately 2 to 10 hours at approximately 80 to 200° C.

The blending may be performed to prepare the plasticizer composition by blending a cyclohexane 1,4-diester-based material converted from the terephthalate-based material through hydrogenation and a citrate-based material at a weight ratio of 1:99 to 99:1, and the cyclohexane 1,4-diester-based material may be a single compound.

The citrate-based material may be prepared through direct esterification between citric acid and one or more alkyl alcohols or transesterification between trialkyl citrate and an alkyl alcohol. The direct esterification may be applied in the same manner as applied to the above-described cyclohexane 1,4-diester-based material, and the transesterification may be performed as to be described below.

The term "transesterification" used herein refers to a reaction between an alcohol and an ester as shown in Reaction Scheme 1, in which R" of the ester is exchanged with R' of the alcohol.

[Reaction Scheme 1]

According to an exemplary embodiment of the present invention, the transesterification may produce three types of ester compositions according to three cases in which an alkoxide of the alcohol attacks carbons of two ester (RCOOR") groups present in an ester-based compound; an alkoxide of the alcohol attacks carbons of one ester (RCOOR") group present in an ester-based compound; and there is no reaction between an alcohol and an ester group in an ester-based compound.

In addition, compared to an acid-alcohol esterification, the transesterification does not cause water contamination, and may solve problems caused by the use of an acidic catalyst because of proceeding without a catalyst.

For example, through the transesterification between tri(2-ethylhexyl) citrate and butyl alcohol, a mixture of tri(2-ethylhexyl) citrate, di(2-ethylhexyl) butyl citrate, dibutyl (2-ethylhexyl) citrate and tributyl citrate may be generated. The mixture includes 3.0 to 70 wt % of tri(2-ethylhexyl) citrate, 0.5 to 50 wt % of two types of citrates having a hybrid alkyl and 0.5 to 85 wt % of tributyl citrate based on a total weight of the mixture. Specifically, the mixture includes 10 to 50 wt % of tri(2-ethylhexyl) citrate, 0.5 to 50 wt % of two types of citrates having a hybrid alkyl and 35 to 85 wt % of tributyl citrate based on a total weight of the mixture. Therefore, in the above ranges, a citrate-based material (mixture) having high process efficiency and excellent processability and an excellent absorption rate may be obtained.

In addition, a composition ratio of the mixture prepared by the transesterification may be controlled according to an amount of the alcohol added.

The amount of the alcohol added may be 0.1 to 89.9 parts by weight, specifically, 3 to 50 parts by weight, and more specifically 5 to 40 parts by weight based on 100 parts by weight of the citrate-based material.

As a larger amount of the alcohol is added, a mole fraction of the citrate participating in the transesterification is higher, and therefore, in the product, the amount of a citrate generated by the attack of only one or two ester groups and the amount of a citrate generated by the attack of three ester groups may be increased.

Accordingly, it may tend to reduce the amount of an unreacted citrate.

According to an exemplary embodiment of the present invention, a molar ratio of the reactants, which are a citrate and an alcohol, may be 1:0.005 to 5.0, 1:0.05 to 2.5, or 1:0.1 to 1.0, and within the range, an ester-based plasticizer composition exhibiting high process efficiency and an excellent effect of improving processability is obtained.

However, the composition ratio of the mixture of the three types of citrates is not limited to the above range, and any one of the three types of citrates may be further added to change the composition ratio. An available mixed composition ratio is as follows.

The ester-based composition prepared by the transesterification may include all of a single attack ester compound, a dual attack ester compound and a reaction residual ester compound, and a composition ratio of the ester-based composition may be controlled according to the amount of the alcohol added.

The transesterification may be performed at 120 to 190° C., preferably 135 to 180° C., and more preferably 141 to 179° C. for 10 minutes to 10 hours, preferably 30 minutes to 8 hours, and more preferably 1 to 6 hours. Within the above temperature and time ranges, a mixture of terephthalate-based materials at a desired composition ratio may be effectively obtained. Here, the reaction time may be calculated from the point of time to reach the reaction temperature after reactants are heated.

The transesterification may be performed without a catalyst, and in some cases, may be performed under an acidic catalyst or metal catalyst, which provides an effect of reducing the reaction time.

The acidic catalyst may be, for example, sulfuric acid, methanesulfonic acid or p-toluenesulfonic acid, and the metal catalyst may be, for example, an organic metal catalyst, a metal oxide catalyst, a metal salt catalyst or a metal itself.

The metal component may include, for example, any one selected from the group consisting of tin, titanium and zirconium, or a mixture of two or more thereof.

In addition, according to an exemplary embodiment of the present invention, the method may further include removing an unreacted alcohol and a reaction by-product such as an ester-based compound through distillation after the transesterification.

The distillation may be, for example, two-step distillation for separating the alcohol and the reaction by-product using a difference in boiling point.

In another example, the distillation may be mixed distillation. In this case, a desired composition ratio of the ester-based plasticizer composition may be relatively and stably ensured. The mixed distillation refers to simultaneous distillation of butanol and a reaction by-product.

Since amounts, types, and mixing ratios of the cyclohexane 1,4-diester-based material and the citrate-based material, which are mixed during the blending have been described above, descriptions thereof will be omitted.

Following the blending, addition of an epoxidized material may be further included. Since amounts and types of the further added epoxidized material have been described above, descriptions thereof will be omitted.

According to another exemplary embodiment of the present invention, a resin composition including the above-described plasticizer composition and a resin is provided.

The resin may be any resin known in the art. For example, the resin may be a mixture of one or more selected from the group consisting of ethylene vinyl acetate, polyethylene, polyketone, polypropylene, polyvinyl chloride, polystyrene, polyurethane, a thermoplastic elastomer and polylactic acid, but the present invention is not limited thereto.

The plasticizer composition may be included at 5 to 150 parts by weight based on 100 parts by weight of the resin.

However, depending on a method of processing the resin composition, a amount of the plasticizer may be changed, and in the case of a resin subjected to melt processing such as extrusion, injection or calendering, the plasticizer may be included at 5 to 100 parts by weight, 5 to 60 parts by weight, or 5 to 50 parts by weight based on 100 parts by weight of the resin.

In addition, in the case of a resin subjected to plastisol processing such as spread coating, spray coating or dip coating, the plasticizer may be included at 30 to 150 parts by weight, 40 to 130 parts by weight, or 60 to 120 parts by weight.

The resin composition may further include a filler. The filler may be included at 0 to 300 parts by weight, preferably, 50 to 200 parts by weight, and more preferably, 100 to 200 parts by weight based on 100 parts by weight of the resin.

The filler may be any filler known in the art without particular limitation. For example, the filler may be a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

In addition, the resin composition may further include other additives such as a stabilizer, etc. as needed. Each of the additives such as a stabilizer, etc. may be, for example, included at 0 to 20 parts by weight, and preferably 1 to 15 parts by weight based on 100 parts by weight of the resin.

The stabilizer may be a calcium-zinc (Ca—Zn)-based stabilizer such as a calcium-zinc composite stearate salt or the like, but the present invention is not limited thereto.

The resin composition may be applied to all of resins used in melt processing and plastisol processing, and for example, may be applied to a compound field such as extrusion or injection, the calendering field and the plastisol field, and products prepared by such processing may be, for example, all types of wires, flooring materials, interior materials for automobile, films, sheets, wallpaper, toys, etc.

EXAMPLES

Hereinafter, to explain the present invention in detail, the present invention will be described in detail with reference to examples. However, examples according to the present invention may be modified in a variety of different forms, and the scope of the present invention should not be construed as being limited to the examples to be described below. The exemplary embodiments of the present invention are provided for those of ordinary skill in the art to more fully understand the present invention.

Preparation Example 1: Preparation of Diisononyl Cyclohexane-1,4-Diester

1) Esterification 498.0 g of purified terephthalic acid (PTA), 1,300 g of isononanol (INA) (molar ratio of PTA:INA—1.0:3.0), and 1.54 g of a titanium-based catalyst (tetra isopropyl titanate (TIPT); 0.31 parts by weight based on 100 parts by weight of PTA) as a catalyst were input into a 3 L 4-neck reaction vessel equipped with a cooler, a condenser, a decanter, a reflux pump, a temperature controller, an agitator, etc., and gradually heated to approximately 170° C. Water started to be generated at approximately 170° C., and esterification was performed for approximately 4.5 hours with continuous addition of nitrogen gas at a reaction temperature of approximately 220° C. under atmospheric pressure and then terminated when an acid value reached 0.01.

After the reaction, to remove unreacted raw materials, distillation extraction was performed for 0.5 to 4 hours under reduced pressure. To remove unreacted raw materials to a predetermined amount level or less, steam extraction was performed using steam for 0.5 to 3 hours under reduced pressure, and neutralization was performed using an alkali solution after a reaction solution was cooled to approximately 90° C. Additionally, washing may be carried out, and then the reaction solution was dehydrated to remove moisture. A filtering material was input into the dehydrated reaction solution, after stirring for a predetermined time and filtering, 1,243 g of diisononyl terephthalate (yield: 99.0%) was obtained.

2) Hydrogenation 1000 g of a composition generated by the esterification and 20 g of a ruthenium catalyst (N.E CHEMCAT) were input as raw materials into a 1.5 L high-pressure reaction vessel, hydrogenation was performed by adding hydrogen under a pressure of 8 MPa at 150° C. for 3 hours, and then the reaction was completed. After the reaction, the catalyst was filtered, and a conventional purification process was performed, thereby preparing a hydrogenated mixed composition with a yield of 99%.

Preparation Example 2: Preparation of Di(2-Propylheptyl) Cyclohexane-1,4-Diester A hydrogenated mixed composition was obtained through esterification and hydrogenation in the same manner as described in Preparation Example 1 using 2-propylheptyl alcohol, instead of isononyl alcohol used in the esterification of Preparation Example 1.

Preparation Example 3: Preparation of TBC

As reaction raw materials, 384 g of citric acid and 580 g of butanol were used to finally obtain 706 g of tributyl citrate (yield: 98%).

Preparation Example 4: Preparation of TOC

As reaction raw materials, 384 g of citric acid and 1014 g of 2-ethylhexanol were used to finally obtain 1029 g of tri-2-ethylhexyl citrate (yield: 98%).

Preparation Example 5: Preparation of TiNC

As reaction raw materials, 384 g of citric acid and 1123 g of isononaol were used to finally obtain 1111 g of triisononyl citrate (yield: 98%).

Preparation Example 6: Preparation of TPHC

As reaction raw materials, 384 g of citric acid and 1235 g of 2-propylheptanol were used to finally obtain 1,200 g of tri(2-propylheptyl)citrate (yield: 98%).

Examples 1 to 8 and Comparative Examples 1 to 10

Compositions of the Examples and Comparative Examples are shown in Table 1 below.

TABLE 1

| Classification | Hydrogenated mixed composition | Citrate-based material | Mixing ratio |
| --- | --- | --- | --- |
| Example 1 | 1,4-DINCH | TBC | 7:3 |
| Example 2 | 1,4-DINCH | TBC | 3:7 |
| Example 3 | 1,4-DINCH | TOC | 8:2 |
| Example 4 | 1,4-DINCH | TOC | 2:8 |
| Example 5 | 1,4-DPHCH | TINC | 6:4 |
| Example 6 | 1,4-DPHCH | TPHC | 6:4 |
| Example 7 | 1,4-DPHCH | TBC | 5:5 |
| Example 8 | 1,4-DPHCH | TOC | 5:5 |
| Comparative Example 1 | 1,4-DEHCH | TOC | 5:5 |
| Comparative Example 2 | 1,4-DHpCH | TBC | 5:5 |
| Comparative Example 3 | 1,4-DBCH | TOC | 5:5 |
| Comparative Example 4 | 1,4-DBenCH | TOC | 5:5 |
| Comparative Example 5 | 1,4-DCyHCH | TBC | 5:5 |
| Comparative Example 6 | 1,2-DEHCH | TOC | 5:5 |
| Comparative Example 7 | 1,2-DINCH | TBC | 5:5 |
| Comparative Example 8 | 1,2-DPHCH | TBC | 5:5 |
| Comparative Example 9 | 1,4-DPHCH | — | — |
| Comparative Example 10 | — | TOC | — |

Examples 9 to 11

To confirm the improvement in thermal resistance using an epoxidized material, compositions of Examples 9 to 11 are shown in Table 2 below.

TABLE 2

| Classification | Plasticizer composition | Epoxidized material | Mixing ratio |
| --- | --- | --- | --- |
| Example 9 | Example 1 | ESO | 7:3 |
| Example 10 | Example 1 | ESO | 5:5 |
| Example 11 | Example 1 | ESO | 4:6 |

Experimental Example 1: Evaluation of Physical Properties

Specimens for an experiment were prepared using the plasticizer compositions of the Examples and Comparative Examples described in Tables 1 and 2.

Each specimen was prepared, according to ASTM D638, by mixing 40 parts by weight of each of the plasticizer compositions of Examples 1 to 11 and Comparative Examples 1 to 5, and 3 parts by weight of a stabilizer (BZ-153T) with 100 parts by weight of PVC (LS100S) using a 3 L super mixer at 98° C. and 700 rpm, forming a 5-mm sheet by roll milling at 160° C. for 4 minutes, performing pressing at 180° C. under low pressure for 2.5 minutes, and under high pressure for 2 minutes, and then forming 1 T and 3 T sheets. Physical properties of each specimen were evaluated by the test items listed below, and the results are summarized in Tables 3 and 4 below.

<Test Items>

Measurement of Hardness

According to ASTM D2240, Shore (shore "A") hardness was measured at 25° C. under 3 T and 10 s conditions.

Measurement of Tensile Strength

According to ASTM D638, each specimen was pulled at a cross head speed of 200 mm/min (1 T) using a tensile testing instrument (U.T.M, Manufacturer; Instron, Model No.: 4466), and a position at which the specimen was broken was detected. A tensile strength was calculated as follows:

Tensile strength (kgf/mm$^2$)=Load value (kgf)/Thickness (mm)×Width (mm)

Measurement of Elongation Rate

According to ASTM D638, each specimen was pulled at a cross head speed of 200 mm/min (1 T) using the U.T.M, and a position at which the specimen was broken was detected. An elongation rate was calculated as follows:

Elongation rate (%)=Length after elongation/Initial length×100

Measurement of Migration Loss

An experimental specimen having a thickness of 2 mm or more was obtained according to KSM-3156, and following attachment of PS plates to both sides of the specimen, a weight of 1 kgf/cm$^2$ was applied to the specimen. The specimen was put in a forced convection drying oven (80° C.) for 72 hours, and cooled at room temperature for 4 hours. Then, after the PSs attached to both sides of the specimen were removed, a weight was measured before and after the specimen was put in the oven and thus a migration loss was calculated by the equation as follows:

Migration loss (%)=[(Initial weight of specimen at room temperature−Weight of specimen after being put into oven)/Initial weight of specimen at room temperature]×100

Measurement of Volatile Loss

The prepared specimen was processed at 80° C. for 72 hours, and a weight of the specimen was measured as follows:

Volatile loss (%)=[(Weight of initial specimen−Weight of specimen after processed)/Weight of initial specimen]×100

Stress Test

A stress test was performed by leaving the specimen at room temperature for predetermined time while bent, and a degree of migration (leaking degree) was observed and quantified. A value closer to 0 indicates a superior property and a value closer to 3 indicates a poor property Thermal Stability Test A 0.5 T specimen prepared through roll-milling was moved at a rate of 10 mm/25 seconds in a 220° C. Mathis oven to test thermal stability of the specimen according to high temperature contact.

TABLE 3

| Classification | Hardness (Shore "A") | Tensile strength (kg/cm$^2$) | Elongation rate (%) | Migration loss (%) | Volatile loss (%) | Stress test |
|---|---|---|---|---|---|---|
| Example 1 | 82.5 | 192.1 | 337.5 | 2.58 | 2.22 | 0.5 |
| Example 2 | 77.5 | 174.6 | 304.6 | 3.56 | 3.40 | 0 |
| Example 3 | 84.0 | 198.5 | 320.1 | 2.56 | 1.88 | 0 |
| Example 4 | 85.5 | 208.7 | 314.2 | 1.21 | 1.20 | 0.5 |
| Example 5 | 85.5 | 220.5 | 320.4 | 1.68 | 1.31 | 0.5 |
| Example 6 | 86.0 | 224.7 | 318.5 | 1.56 | 1.11 | 0.5 |
| Example 7 | 80.0 | 198.6 | 325.6 | 2.54 | 2.43 | 0 |
| Example 8 | 85.0 | 211.1 | 308.4 | 2.86 | 1.77 | 0.5 |
| Comparative Example 1 | 84.0 | 185.3 | 287.4 | 3.57 | 2.48 | 2.0 |
| Comparative Example 2 | 78.5 | 168.4 | 267.1 | 4.88 | 4.50 | 1.5 |
| Comparative Example 3 | 82.0 | 170.5 | 271.3 | 5.66 | 6.58 | 2.0 |
| Comparative Example 4 | 87.0 | 200.7 | 295.4 | 3.56 | 1.50 | 3.0 |
| Comparative Example 5 | 83.5 | 178.5 | 288.0 | 3.60 | 3.20 | 1.5 |
| Comparative Example 6 | 83.0 | 187.0 | 290.3 | 4.11 | 3.87 | 0.5 |
| Comparative Example 7 | 81.0 | 174.5 | 268.4 | 5.24 | 5.79 | 0.5 |
| Comparative Example 8 | 83.5 | 180.2 | 288.0 | 5.60 | 5.81 | 1.0 |
| Comparative Example 9 | 85.0 | 165.5 | 274.3 | 3.60 | 3.47 | 2.0 |
| Comparative Example 10 | 87.5 | 172.3 | 290.2 | 3.10 | 2.58 | 2.5 |

TABLE 4

| Division | Hardness (Shore "A") | Tensile strength (kg/cm$^2$) | Elongation rate (%) | Migration loss (%) | Volatile loss (%) | Stress test |
|---|---|---|---|---|---|---|
| Example 9 | 82.5 | 214.5 | 348.0 | 2.20 | 1.76 | 0 |
| Example 10 | 83.0 | 228.4 | 345.8 | 1.62 | 1.22 | 0 |
| Example 11 | 84.5 | 208.7 | 314.2 | 1.22 | 1.01 | 1.5 |

Referring to Table 3, in Comparative Examples 1 to 5 in which a cyclohexane 1,4-diester-based material had less than 9 carbon atoms, compared with the examples in which the same citrate-based material was added, it can be confirmed that these comparative examples exhibited very poor physical properties such as migration loss and volatile loss as well as mechanical properties such as tensile strength and an elongation rate. In addition, it can be confirmed that, since the compositions in these comparative examples generally have a low resistance to stress, the plasticizer in the resin is easily effused.

In addition, when a material in which a diester group is bound at the 1,2-positions, rather than a diester group being bound at the 1,4-positions, was used, it can be more obvious that physical properties such as tensile strength, an elongation rate, migration loss and volatile loss were poorer than the effects due to the carbon number.

Accordingly, in all aspects of the mechanical properties (the tensile strength and the elongation rate), and the physical properties relating to the total weight of the plasticizer (the migration loss and the volatile loss), to prepare a resin having satisfactory physical properties, it was confirmed that the cyclohexane 1,4-diester-based material is preferably mixed with a citrate-based material using an alkyl group having 9 or more carbon atoms.

In addition, referring to Table 4, it can be confirmed that Examples 9 to 11 are prepared by adding epoxidized soybean oil to Example 1 at ratios of 7:3, 5:5 and 4:6, respectively, and as an epoxidized material is added, the volatile loss and the migration loss become excellent, and the mechanical properties such as the tensile strength, the elongation rate, etc. can be ensured at high levels.

However, when a very large amount of the epoxidized material is used, as shown in Example 11, the mechanical properties such as the elongation rate or the tensile strength may be drastically reduced, and the resistance to stress may be degraded, therefore, it is preferable that the epoxidized material is included at 100 parts by weight or less based on 100 parts by weight of the mixture of the cyclohexane 1,4-diester-based material and the citrate-based material.

Further, referring to FIG. 1, while it can be confirmed that, in Examples 1 and 5 in which the epoxidized material is not added, the specimen was burned and appeared almost black, in Example 9, almost no discoloration was visually detected, and therefore the thermal stability can be improved by addition of the epoxidized material.

That is, it can be concluded that all physical properties are improved when the epoxidized material is mixed at 10 parts by weight or more to serve as a "plasticizer," not as a subsidiary stabilizer.

A plasticizer composition according to an exemplary embodiment of the present invention, when used in a resin composition, can provide excellent physical properties such as migration resistance, volatility resistance, etc., as well as excellent plasticization efficiency, tensile strength and an excellent elongation rate.

While the present invention has been described in detail with reference to exemplary embodiments of the present invention, it should be understood to those of ordinary skill in the art that the scope of the present invention is not limited thereto, and also includes various forms of modification and alternation based on the fundamental ideas of the present invention defined by the accompanying claims.

What is claimed is:

1. A plasticizer composition, comprising:
   a cyclohexanoate component consisting of one kind of cyclohexane 1,4-diester-based material; and
   a citrate-based material,
   wherein a weight ratio of the cyclohexanoate component and the citrate-based material is from 80:20 to 20:80; and
   wherein the citrate-based material is a citrate in which an acetyl group is not included, and the citrate-based material is tri(2-ethylhexyl) citrate (TOC), and
   wherein the cyclohexane 1,4-diester-based material is diisononyl cyclohexane-1,4-diester (1,4-DINCH).

2. The plasticizer composition of claim 1, wherein the weight ratio of the cyclohexane 1,4-diester-based material and the citrate-based material is from 80:20 to 50:50.

3. The plasticizer composition of claim 2, wherein the weight ratio of the cyclohexane 1,4-diester-based material and the citrate-based material is from 80:20 to 60:40.

4. The plasticizer composition of claim 1, further comprising an epoxidized material.

5. The plasticizer composition of claim 4, wherein the epoxidized material is further comprised in an amount of 1 to 100 parts by weight based on 100 parts by weight of the sum of the cyclohexane 1,4-diester-based material and the citrate-based material.

6. The plasticizer composition of claim 4, wherein the epoxidized material comprises one or more selected from the group consisting of epoxidized soybean oil, epoxidized castor oil, epoxidized linseed oil, epoxidized palm oil, an epoxidized stearate, an epoxidized oleate, an epoxidized tallate and an epoxidized linoleate.

7. A resin composition comprising:
   100 parts by weight of a resin; and
   5 to 150 parts by weight of the plasticizer composition of claim 1.

8. The resin composition of claim 7, wherein the resin comprises one or more selected from the group consisting of ethylene vinyl acetate, polyethylene, polypropylene, polyketone, polyvinyl chloride, polystyrene, polyurethane, and a thermoplastic elastomer.

9. A plasticizer composition, comprising:
   a cyclohexanoate component consisting of one kind of cyclohexane 1,4-diester-based material; and
   a citrate-based material,
   wherein a weight ratio of the cyclohexanoate component and the citrate-based material is from 80:20 to 20:80; and
   wherein the citrate-based material is a citrate in which an acetyl group is not included, and the citrate-based material is tri(2-ethylhexyl) citrate (TOC); and
   wherein the cyclohexane 1,4-diester-based material is di(2-propylheptyl) cyclohexane-1,4-diester (1,4-DPHCH).

10. The plasticizer composition of claim 9, wherein the weight ratio of the cyclohexane 1,4-diester-based material and the citrate-based material is from 80:20 to 50:50.

11. The plasticizer composition of claim 10, wherein the weight ratio of the cyclohexane 1,4-diester-based material and the citrate-based material is from 80:20 to 60:40.

12. The plasticizer composition of claim 9, further comprising an epoxidized material.

13. The plasticizer composition of claim 12, wherein the epoxidized material is further comprised in an amount of 1 to 100 parts by weight based on 100 parts by weight of the sum of the cyclohexane 1,4-diester-based material and the citrate-based material.

14. The plasticizer composition of claim 12, wherein the epoxidized material comprises one or more selected from the group consisting of epoxidized soybean oil, epoxidized castor oil, epoxidized linseed oil, epoxidized palm oil, an epoxidized stearate, an epoxidized oleate, an epoxidized tallate and an epoxidized linoleate.

* * * * *